United States Patent
Gillberg et al.

(12) 
(10) Patent No.: US 6,538,035 B2
(45) Date of Patent: Mar. 25, 2003

(54) USE OF TOLTERODINE TO TREAT ASTHMA

(75) Inventors: Per-Goran Gillberg, Uppsala (SE);
Staffan Sundquist, Huskvarna (SE);
Sue K. Cammarata, Portage, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 10/045,135

(22) Filed: Oct. 23, 2001

(65) Prior Publication Data

US 2002/0161054 A1 Oct. 31, 2002

Related U.S. Application Data

(60) Provisional application No. 60/242,899, filed on Oct. 24, 2000, provisional application No. 60/283,120, filed on Apr. 11, 2001, and provisional application No. 60/314,218, filed on Aug. 22, 2001.

(51) Int. Cl.$^7$ .............................................. A61K 31/135
(52) U.S. Cl. ..................... 514/650; 514/649; 514/642; 514/643
(58) Field of Search .................................. 514/642, 643, 514/649, 650

(56) References Cited

U.S. PATENT DOCUMENTS

| 5,382,600 A | 1/1995 | Jonsson et al. | 514/603 |
| 5,559,269 A | 9/1996 | Johansson et al. | 564/443 |
| 6,124,354 A | 9/2000 | Akerblom et al. | 514/438 |

FOREIGN PATENT DOCUMENTS

| WO | WO/98/29402 | 12/1997 | C07D/311/20 |

OTHER PUBLICATIONS

R.A.B.Bannard, J.H.Parkkari, I.W.Coleman, "Preparation of Antidotes for Anticholinesterase Poisoning", Canada Journal of Chemistry, 40, 1962, pp 1909–1916.

L. Nilvebrant, PG Gillberg, B. Sparf, "Antimuscarinic Potency and Bladder Selectivity of PNU–200577, a Major Metabolite of Tolterodine", Pharmacol. Toxicology, 81, 1997, pp. 169–172.

HPostlind, ADanielson, ALindgren, SHGAndersson, "Tolterodine, a New Muscarinic Receptor Antagonist, Is Metabolized by Cytochromes P450 2D6 and 3A in Human Liver Microsomes", Drug Metabolism and Disposition, 26(4), 1998, pp 289–293.

C.H.Tilford, M.G. Van Campen, Jr., R.S.Shelton, "Aminoesters of Substituted Alicylic Carboxylic Acids", Journal of American Chemical Society, 69, 1947, pp 2902–2906.

*Primary Examiner*—Theodore J. Criares
(74) *Attorney, Agent, or Firm*—Austin W. Zhang

(57) ABSTRACT

The present invention is a method of treating an mammal selected from the group consisting of humans and horses who has asthma, COPD or allergic rhinitis and is in need of such treatment by inhaling an anti-asthma, anti-COPD anti-allergic rhinitis effective amount, respectively, of a compound selected from the group consisting of tolterodine

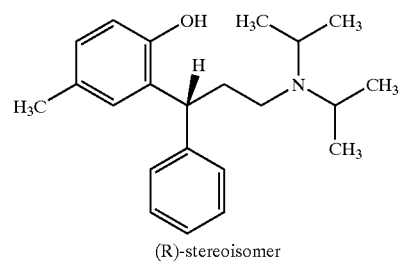

(R)-stereoisomer hydroxytolterodine and 2-(diisopropylamino)ethyl-1-phenylcyclopentanecarboxylate and pharmaceutically acceptable salts thereof.

24 Claims, No Drawings

USE OF TOLTERODINE TO TREAT ASTHMA

CROSS-REFERENCE TO RELATED APPLICATIONS

This application claims the benefit of U.S. Provisional Patent Application Ser. Nos. 60/242,899 filed Oct. 24, 2000, 60/283,120 filed Apr. 11, 2001, 60/314,218 filed Aug. 22, 2001, under 35 USC 119(e)(i). The entire disclosure of which is herein incorporated by reference.

BACKGROUND OF THE INVENTION

1. Field of the Invention

The present invention is a new use for tolterodine and a few other similar compounds to treat asthma, a group of breathing disorders termed Chronic Obstructive Pulmonary Disease (COPD) and allergic rhinitis.

2. Description of the Related Art

U.S. Pat. No. 5,382,600 discloses 2-[(1R)-3-(diisopropylamino)-1-phenylpropyl]-4-methylphenol also known as N,N-diisopropyl-3-(2-hydroxy-5-methylphenyl)-3-phenylpropylamine with the generic name of tolterodine as being useful to treat urinary incontinence. *Drug Metabolism and Disposition*, 26(4), 289–293 (1998) discloses that tolterodine is a muscarinic receptor antagonist.

U.S. Pat. No. 5,559,269 and *Drug Metabolism and Disposition*, 26(4), 289–293 (1998) disclose hydroxytolterodine. U.S. Pat. No. 5,559,269 discloses this compound as useful to treat urinary incontinence. *Pharmacol. Toxicol.*, 81, 169–172 (1997) discloses that hydroxytolterodine has antimuscarinic activity.

U.S. Pat. No. 6,124,354 discloses 2-(diisopropylamino)ethyl-1-phenylcyclopentanecarboxylate, see Example 99, and its use in treating urinary incontinence and irritable bowel syndrome. *Can. J. Chem.*, 40, 1909–1916 (1962) refers to this compound as a potential antidote for treatment of anticholinesterase poisoning. *J. Am. Chem. Soc.*, 69, 2902–2906 (1947) while not mentioning the diisopropylamino compound but a diethylamino analog, discusses that the diethylamino compound has antispasmolytic action against acetylcholine.

It is known that antimuscarinic compounds are used in the treatment of asthma and COPD.

The antimuscarinic compound ipratroprium has been approved for use in treating allergic rhinitis.

SUMMARY OF INVENTION

Disclosed is a method of treating a mammal selected from the group consisting of humans and horses that have asthma and are in need of such treatment by inhaling an anti-asthma effective amount of a compound selected from the group consisting of tolterodine, hydroxytolterodine and 2-(diisopropylamino)ethyl-1-phenylcyclopentanecarboxylate or a pharmaceutically acceptable salt thereof.

Also disclosed is a method of treating a mammal selected from the group consisting of humans and horses that have COPD and are in need of such treatment by inhaling an anti-COPD effective amount of a compound selected from the group consisting of tolterodine, hydroxytolterodine and 2-(diisopropylamino)ethyl-1-phenylcyclopentanecarboxylate or a pharmaceutically acceptable salts thereof.

Further disclosed is a method of treating a mammal selected from the group consisting of humans and horses that has allergic rhinitis and is in need of such treatment by inhaling an anti-allergic rhinitis effective amount of a compound selected from the group consisting of tolterodine, hydroxytolterodine and 2-(diisopropylamino)ethyl-1-phenylcyclopentanecarboxylate or a pharmaceutically acceptable salt thereof.

DETAILED DESCRIPTION OF THE INVENTION

U.S. Pat. No. 5,382,600 discloses tolterodine (Example 22) and that it is useful to treat urinary incontinence. Tolterodine is presently being sold in a number of different countries for that purpose. When tolterodine is used to treat urinary incontinence it is administered orally. It is preferred that tolterodine be prepared by the process of International Publication WO98/29402.

Hydroxytolterodine and 2-(diisopropylamino)ethyl-1-phenylcyclopentanecarboxylate are also known compounds. For convenience, these three compounds collectively will be referred to as ANTI-ASTHMA/ANTI-COPD/ANTI-ALLERGIC RHINITIS AGENTS. It is preferred that the ANTI-ASTHMA/ANTI-COPD/ANTI-ALLERGIC RHINITIS AGENT be tolterodine.

The present invention is the use of the ANTI-ASTHMA/ANTI-COPD/ANTI-ALLERGIC RHINITIS AGENTS to treat asthma, COPD and allergic rhinitis.

The method of the present invention is used to treat mammals including humans and horses. It is preferred that the mammal be a human.

The compounds of the present invention are administered by inhalation. The inhalation can be by either an aerosol or a powder.

An anti-asthma, anti-COPD and anti-allergic rhinitis effective amount of ANTI-ASTHMA/ANTI-COPD/ANTI-ALLERGIC RHINITIS AGENTS is from about 0.05 mg to about 12 mg. It is preferred that the anti-asthma, anti-COPD and anti-allergic rhinitis effective amount is from about 0.1 to about 6 mg; it is more preferred that the anti-asthma, anti-COPD and anti-allergic rhinitis effective amount is from about 0.2 to about 5 mg.

The ANTI-ASTHMA/ANTI-COPD/ANTI-ALLERGIC RHINITIS AGENTS can be administered from one thru four times daily. It is preferable to administer the ANTI-ASTHMA/ANTI-COPD/ANTI-ALLERGIC RHINITIS AGENTS two or three times daily, more preferable twice daily.

The minimum amount of an aerosol delivery is about 0.2 ml and the maximum aerosol delivery is about 5 ml. The concentration of the ANTI-ASTHMA/ANTI-COPD/ANTI-ALLERGIC RHINITIS AGENTS is not critical so long as the total amount of spray delivered is within the about 0.2 to about 5 ml amount and it delivers an anti-asthma, anti-COPD and anti-allergic rhinitis effective amount. It is well known to those skilled in the art that if the concentration is higher, one gives a smaller dose to deliver the same "effective amount". The non-active ingredient or carrier can be (sterile) water with the pH adjusted to where the active anti-asthma pharmaceutical agent is very soluble. It is preferred that the pH be at or near 7. Alternatively and preferably, the non-active carrier agent should be physiological saline with the pH adjusted appropriately. Aerosols for inhalation of various pharmaceutical agents are well known to those skilled in the art including many aerosols for treating asthma, COPD and allergic rhinitis. There is nothing special in the present invention regarding the aerosol.

Alternatively the dosage form for inhalation can be a powder. Powders for inhalation of various pharmaceutical agents are well known to those skilled in the art including many powders for treating asthma, COPD and allergic rhinitis. There is nothing special in the present invention regarding the powder. When the dosage form is a powder, the active pharmaceutical agent can be administered in pure form or diluted with an inert carrier. When an inert carrier is used, the ANTI-ASTHMA/ANTI-COPD/ANTI-ALLERGIC RHINITIS AGENT pharmaceutical agent is compounded such that the total amount of powder delivered delivers an "effective amount" of the ANTI-ASTHMA/ANTI-COPD/ANTI-ALLERGIC RHINITIS AGENT. The actual concentration of the ANTI-ASTHMA/ANTI-COPD/ANTI-ALLERGIC RHINITIS AGENT is not critical. If the concentration is lower, then more powder must be delivered; if the concentration is higher, less total material must be delivered to provide an effective amount of one of the ANTI-ASTHMA/ANTI-COPD/ANTI-ALLERGIC RHINITIS AGENTS.

Various devices are on the market for administering powders for inhalation for asthma, COPD and allergic rhinitis and these devices are suitable for administering the compounds of the present invention.

Pharmaceutically acceptable salts include salts of both inorganic and organic acids. The pharmaceutically acceptable salts are preferred over the corresponding free amines since they produce compounds that are more water soluble and more crystalline. The preferred pharmaceutically acceptable salts include salts of the following acids hydrochloric, hydrobromic, sulfuric, phosphoric, nitric, citric, methanesulfonic $CH_3—(CH_2)_{n1}—COOH$ where $n_1$ is 0 thru 4, $HOOC—(CH_2)n_1—COOH$ where n is as defined above, $HOOC—CH=CH—COOH$, $\phi\text{-}COOH$. For other acceptable salts, see *Int. J. Pharm.*, 33, 201–217 (1986).

DEFINITIONS

All temperatures are in degrees Celsius.

COPD refers to Chronic Obstructive Pulmonary Disease.

Allergic rhinitis refers to acute rhinitis or nasal rhinitis.

Tolterodine refers to 2-[(1R)-3-(diisopropylamino)-1-phenylpropyl]-4-methylphenol also known as N,N-diisopropyl-3-(2-hydroxy-5-methylphenyl)-3-phenylpropylamine, a compound of the formula:

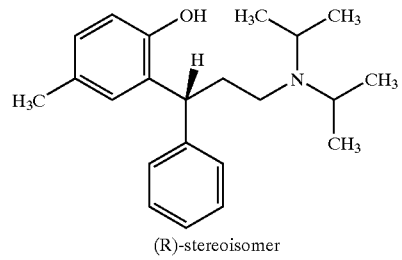

(R)-stereoisomer

Hydroxytolterodine refers to 2-[(1R)-3-(diisopropylamino)-1-phenylpropyl]-4-(hydroxymethyl)phenol, a compound of the formula:

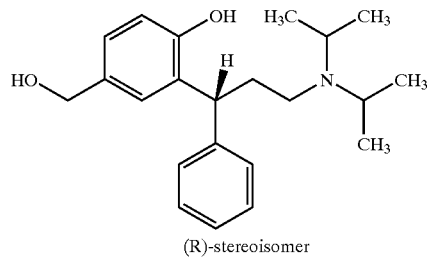

(R)-stereoisomer

2-[Bis(1-methylethyl)amino]ethyl-1-phenylcyclopentanecarboxylate also known as 2-(diisopropylamino)ethyl-1-phenylcyclopentanecarboxylate, a compound of the formula:

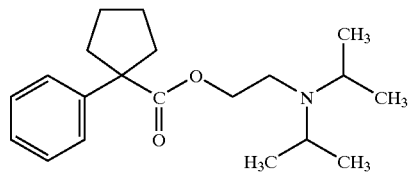

ANTI-ASTHMA/ANTI-COPD/ANTI-ALLERGIC RHINITIS AGENTS refers to tolterodine, hydroxytolterodine and 2-(diisopropylamino)ethyl-1-phenylcyclopentanecarboxylate.

Physiological saline refers to a 0.9% aqueous sodium chloride solution.

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

When solvent pairs are used, the ratios of solvents used are volume/volume (v/v).

When the solubility of a solid in a solvent is used the ratio of the solid to the solvent is weight/volume (wt/v).

$FEV_1$ refers to Force Expiratory Volume in one second.

$FEV_1/FVC$ refers to the ratio of the Force Expiratory Volume/Force Vital Capacity.

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

Example 1

A 65 year old female with a history of chronic COPD with $FEV_1$ of 1.5 liters is treated with tolterodine aerosol 1 mg every 12 hr continuously for dyspnea. After two weeks of therapy dyspnea tolerance is improved.

Example 2

A 50 year old male with a history of chronic COPD with $FEV_1/FVC$ of 60% liters is treated with hydroxytolterodine aerosol 2 mg every 8 hr continuously for dyspnea. After a week of treatment the $FEV_1/FVC$ ratio improves to about 65%.

Example 3

A 25 year old female with a history of asthma with a morning peak flow of less than 2 l/sec is treated with 2-(diisopropylamino)ethyl-1-phenylcyclopentanecarboxylate powder 0.1 mg every 8 hr continuously. Treatment improves the peak flow to 4–5 l/sec.

Example 4

A 35 year old male with a history of severe asthma with a morning peak flow of 5 l/sec is treated with tolterodine powder 6 mg once a day continuously. After a week of treatment the peak flow improves to 9 l/sec.

Example 5

A 45 year old female with a history of severe asthma with a morning peak flow of less than 3 l/sec is treated with tolterodine aerosol 2 mg three times daily continuously. After a week of treatment the peak flow improves to 6 l/sec.

What is claimed is:

1. A method of treating a mammal selected from the group consisting of humans and horses that have asthma and are in need of such treatment by inhaling an anti-asthma effective amount of a compound selected from the group consisting of tolterodine, hydroxytolterodine and 2-(diisopropylamino)ethyl-1-phenylcyclopentanecarboxylate or a pharmaceutically acceptable salt thereof.

2. A method of treatment according to claim 1 where the mammal is a human.

3. A method of treatment according to claim 1 where the inhalation is with an aerosol.

4. A method of treatment according to claim 1 where the inhalation is with a powder.

5. A method of treatment according to claim 1 where the anti-asthma effective amount is from about 0.05 mg to about 12 mg.

6. A method of treatment according to claim 5 where the anti-asthma effective amount is from about 0.1 to about 6 mg.

7. A method of treatment according to claim 6 where the anti-asthma effective amount is from about 0.2 to about 5 mg.

8. A method of treatment according to claim 1 where the compound is tolterodine.

9. A method of treating a mammal selected from the group consisting of humans and horses that have COPD and are in need of such treatment by inhaling an anti-COPD effective amount of a compound selected from the group consisting of tolterodine, hydroxytolterodine and 2-(diisopropylamino)ethyl-1-phenylcyclopentanecarboxylate or a pharmaceutically acceptable salt thereof.

10. A method of treatment according to claim 9 where the mammal is a human.

11. A method of treatment according to claim 8 where the inhalation is with an aerosol.

12. A method of treatment according to claim 11 where the inhalation is with a powder.

13. A method of treatment according to claim 9 where the anti-asthma effective amount is from about 0.05 mg to about 12 mg.

14. A method of treatment according to claim 13 where the anti-asthma effective amount is from about 0.1 to about 6 mg.

15. A method of treatment according to claim 14 where the anti-asthma effective amount is from about 0.2 to about 5 mg.

16. A method of treatment according to claim 9 where the compound is tolterodine.

17. A method of treating a mammal selected from the group consisting of humans and horses that have allergic rhinitis and are in need of such treatment by inhaling an anti-allergic rhinitis effective amount of a compound selected from the group consisting of tolterodine, hydroxytolterodine and 2-(diisopropylamino)ethyl-1-phenylcyclopentanecarboxylate or a pharmaceutically acceptable salt thereof.

18. A method of treatment according to claim 17 where the mammal is a human.

19. A method of treatment according to claim 17 where the inhalation is with an aerosol.

20. A method of treatment according to claim 1 where the inhalation is with a powder.

21. A method of treatment according to claim 1 where the anti-allergic rhinitis effective amount is from about 0.05 mg to about 12 mg.

22. A method of treatment according to claim 21 where the anti-allergic rhinitis effective amount is from about 0.1 to about 6 mg.

23. A method of treatment according to claim 6 where the anti-allergic rhinitis effective amount is from about 0.2 to about 5 mg.

24. A method of treatment according to claim 17 where the compound is tolterodine.

* * * * *